United States Patent [19]
Lundberg

[11] 3,983,122
[45] Sept. 28, 1976

[54] PROCESS FOR THE PREPARATION OF QUINOLIZINONE DERIVATIVES

[75] Inventor: Charles Andrew Lundberg, Cincinnati, Ohio

[73] Assignee: Richardson-Merrell Inc., Wilton, Conn.

[22] Filed: May 2, 1975

[21] Appl. No.: 574,100

Related U.S. Application Data

[63] Continuation-in-part of Ser. No. 350,384, Dec. 23, 1974, abandoned.

[52] U.S. Cl. ............... 260/289 AZ; 260/283 R; 260/289 D; 260/289 C; 424/258
[51] Int. Cl.² ............................... C07D 487/04
[58] Field of Search ............... 260/289 AZ, 289 C

[56] References Cited
OTHER PUBLICATIONS
Von Strandtmann et al., J. Org. Chem., vol. 31, pp. 797–803, (1966).

*Primary Examiner*—Nicholas S. Rizzo
*Assistant Examiner*—Mary C. Vaughn
*Attorney, Agent, or Firm*—L. Ruth Hattan; Eugene O. Retter; George W. Rauchfuss, Jr.

[57] ABSTRACT

Novel process for the preparation of compounds of the following general structure which are useful as antidepressant and antiparkinson agents:

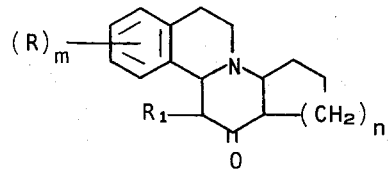

wherein R represents hydrogen, hydroxy, halogen, trifluoromethyl, straight or branched lower alkyl of from 1 to 6 carbon atoms or straight or branched lower alkoxy of from 1 to 6 carbon atoms; $R_1$ represents hydrogen, lower alkyl of from 1 to 6 carbon atoms, phenyl or benzyl; $n$ is an integer of from 1 to 3; $m$ is an integer of 1 or 2; and individual optical and geometric isomers and pharmaceutically acceptable acid addition salts thereof.

10 Claims, No Drawings

PROCESS FOR THE PREPARATION OF QUINOLIZINONE DERIVATIVES

This application is a continuation-in-part of U.S. patent application Ser. No. 350,384 filed Dec. 23, 1974, now abandoned.

FIELD OF INVENTION

This invention relates to a novel process for the preparation of quinolizinone derivatives which are useful as antidepressant and antiparkinson agents and are also useful as starting materials for the preparation of the corresponding quinolizinol compounds which are useful as antidepressants and antiparkinson agents.

DESCRIPTION OF PRIOR ART

A. I. Meyers et al., Tetrahedron Letters 1965, 155–60, describe a method of preparing 2,3,4,4a,6,7,11b,12,13,13a-decahydro-1H-dibenzo[a,f]quinolizin-13-one and 1,2,3,3a,5,6,10b,11,12,12a-decahydrobenzo[a]cyclopenta[f]quinolizin-12-one, that is, wherein R and $R_1$ are hydrogen and n is respectively 2 and 1, which comprises reacting a tetrahydroisoquinoline ester with either cyclohexanone or cyclopentanone and cyclizing the resulting enamine to the enaminoketone which is subsequently reduced with lithium aluminum hydride to give the ketone product. Meyers' method of synthesis is different from the process of the present invention which is a one step reaction involving starting materials that are different from those disclosed by Meyers, et al. Meyers describes no pharmacological utility for the compounds.

SUMMARY OF INVENTION

The novel process of this invention comprises reacting an appropriately substituted 3,4-dihydroisoquinoline derivative with a 1-cycloalk-1-enyl alkyl ketone or a 1-cycloalk-1-enyl aralkyl ketone wherein the 1-cycloalk-1-enyl moiety of each ketone derivative contains from 5 to 7 carbon atoms; the alkyl moiety contains from 1 to 7 carbon atoms, such as, for example, methyl, ethyl, propyl, isopropyl, butyl, pentyl, isopentyl, and heptyl; the aralkyl moiety represents benzyl or phenethyl.

DETAILED DESCRIPTION OF INVENTION

The compounds of the following general Formula I

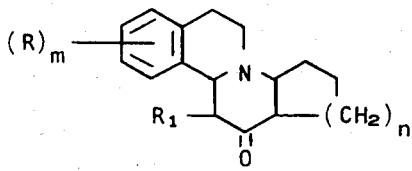

Formula I wherein R represents hydrogen, hydroxy, halogen, trifluoromethyl, straight or branched lower alkyl of from 1 to 6 carbon atoms or straight or branched lower alkoxy of from 1 to 6 carbon atoms; $R_1$ represents hydrogen, lower alkyl of from 1 to 6 carbon atoms, phenyl or benzyl; m is an integer of 1 to 2; and n is an integer of from 1 to 3; are prepared by reacting a 3,4-dihydroisoquinoline derivative of the formula

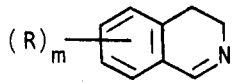

Formula II wherein R and m have the meanings defined hereinabove with a cycloalk-1-enyl derivative of the formula

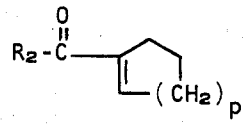

Formula III wherein $R_2$ represents lower alkyl of from 1 to 7 carbon atoms, benzyl or phenethyl, and p is an integer of from 1 to 3.

The above reaction may be carried out with or without a solvent. Suitable solvents for this reaction are lower alcohols, for example, methanol, ethanol, isopropyl alcohol, n-butanol; dimethyl formamide; dimethylsulfoxide; aromatic solvents, such as, for example, benzene, toluene, xylene, and the like; and halogenated hydrocarbon solvents, such as, for example, chloroform. This reaction may be carried out in the presence of an acid catalyst such as, hydrochloric acid or p-toluenesulfonic acid. Preferably one equivalent of the acid catalyst is employed. The reaction time may vary from about 30 minutes to about 60 hours depending upon the reactants, the solvent employed, if any, and the reaction temperature which may vary from about 20° to about 150°C. The product obtained on work-up may be isolated as the free base or the acid addition salt.

A preferred procedure for preparing the compounds of general Formula I is to combine the reactants represented by Formulas II and III in a refluxing lower alcohol solvent, such as, ethanol for from 8 to 48 hours in the presence of an acid catalyst, such as, hydrochloric acid.

As examples of straight or branched lower alkyl groups which R may represent in general Formulas I and II there may be mentioned, for example, methyl, ethyl, propyl, isopropyl, tert-butyl, pentyl and hexyl.

As examples of straight or branched lower alkoxy groups which R may represent in general formulas I and II there may be mentioned, for example, methoxy, ethoxy, propoxy, isopropoxy, butoxy, tert-butoxy, pentoxy.

The term lower alcohol as used herein is taken to mean an aliphatic alcohol containing from 1 to 6 carbon atoms.

As examples of lower alkyl groups which $R_1$ in Formula I and $R_2$ in Formula III may represent there may be mentioned, for example methyl, ethyl, n-propyl, isopropyl, butyl, pentyl, isobutyl, hexyl, and $R_2$ may also be heptyl.

A preferred embodiment of this invention is the reaction, as described above, of a 3,4-dihydroisoquinoline derivative of Formula II wherein m is the integer 1 with a cycloalk-1-enyl derivative of Formula III.

Another preferred embodiment of this invention is the reaction, as described above, of a 3,4-dihydroisoquinoline derivative of Formula II wherein the substituents on the dihydroisoquinoline, as represented by R, are attached at the 6 and 7- positions of the dihydroisoquinoline as represented by the structure

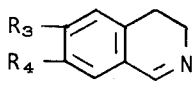

Formula II (a)

and wherein each of the substituents as represented by $R_3$ and $R_4$ is selected from hydrogen, chlorine, fluorine, bromine, iodine, hydroxy, straight or branched lower alkoxy of from 1 to 4 carbon atoms, straight or branched lower alkyl of from 1 to 4 carbon atoms, and trifluoromethyl with the proviso that each of the substituent groups is not trifluoromethyl, that is, when one of the $R_3$ or $R_4$ is trifluoromethyl, the other of $R_3$ or $R_4$ is other than trifluoromethyl with a cycloalk-1-enyl derivative of Formula III.

Another preferred embodiment of this invention is the reaction as described above of a 3,4-dihydroisoquinoline derivative as represented by Formula II (a) wherein the alkyl substituent of from 1 to 4 carbon atoms is straight chained with a cycloalk-1-enyl derivative of Formula III.

Another preferred embodiment of this invention is the reaction as described above of a 3,4-dihydroisoquinoline derivative as represented by general Formula II (a) wherein $R_3$ is hydrogen and $R_4$ is selected from hydrogen, chlorine, fluorine, bromine, iodine, hydroxy, straight or branched lower alkoxy of from 1 to 4 carbon atoms, straight or branched lower alkyl of from 1 to 4 carbon atoms and trifluoromethyl with a cycloalk-1-enyl derivative of Formula III.

Another preferred embodiment of this invention is the reaction as described above of a 3,4-dihydroisoquinoline derivative as represented by Formula II (a) wherein $R_4$ is hydrogen and $R_3$ is selected from chlorine, fluorine, bromine, iodine, hydroxy, straight or branched lower alkoxy of from 1 to 4 carbon atoms, straight or branched lower alkyl of from 1 to 4 carbon atoms and trifluoromethyl, with a cycloalk-1-enyl derivative of Formula III.

The 3,4-dihydroisoquinoline derivatives as represented by Formulas II and II (a) which find use in the above described process may be prepared by reacting an appropriately substituted phenethylamine of the following Formula IV, or for uniformity of representation in reference to the preferred embodiments of Formula II (a), as represented by Formula IV (a)

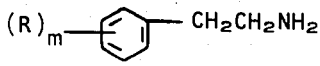

Formula IV

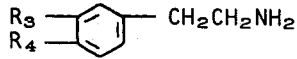

Formula IV (a)

wherein R, $R_3$, $R_4$ and m have the meanings defined hereinabove, with formic acid or alkyl formate followed by dehydration with, for example, polyphosphoric acid or phosphorous oxychloride.

The ketone derivatives as represented by general Formula III which find use in the above described process may be prepared by several methods, for example, by a Friedel-Crafts acylation of a cycloalkene compound containing from 5 to 7 carbon atoms with an acylating agent of the formula

Formula V wherein X represents bromine or chlorine and $R^2$ has the meaning defined hereinabove, followed by dehydrohalogenation with a high boiling tertiary amine such as N,N-di-ethylaniline.

Compounds of Formula III wherein $R^2$ is methyl may also be prepared by reacting a 1-ethynylcycloalkanol derivative, wherein the cycloalkanol moiety contains from 5 to 7 carbon atoms, with phosphorous pentoxide in refluxing benzene or, the 1-ethynylcycloalkanol derivative may be reacted with phosphorous oxychloride in pyridine to give a 1- ethynyl -1-cycloalkene derivative which is subsequently hydrated with, for example, mercuric sulfate catalyst.

There are a number of general procedures for preparing the appropriately substituted phenethylamines known in the art as for example, the procedure described by E. F. Kiefer, J. Med. Chem. 15, 214 (1972) whereby an appropriately substituted benzyl alcohol is treated with a hydrohalo acid, for example, hydrochloric acid to give the corresponding benzyl halide which is treated with sodium cyanide to give the corresponding nitrile derivative. The nitrile derivative is reduced with a mixture of lithium aluminum hydride and aluminum chloride to give the appropriately substituted phenethylamine. The appropriately substituted benzylhalide intermediate wherein the substituents on the benzyl halide do not contain a benzylic proton may be obtained by halogenation of the corresponding tolyl derivative by the action of N-bromo- or N-chlorosuccinamide by procedures generally known in the art. The appropriately substituted benzyl alcohol derivative may be obtained by reduction of the corresponding carboxylic acid or lower alkyl ester thereof or the corresponding benzaldehyde by, for example, lithium aluminum hydride reduction. The appropriately substituted benzoic acid derivative may be obtained from the corresponding nitro or amine derivative by standard methods, for example, the nitro derivative can be reduced with tin and hydrochloric acid to give the corresponding amine which is diazotized with for example, nitrous acid followed by reaction with cuprous cyanide with subsequent aqueous acid hydrolysis to give the corresponding carboxylic acid.

Most of the starting materials used to prepare the appropriately substituted phenethylamines are commercially available, or known in the art, or can be prepared by procedures known in the art, as for example, those described above. The higher alkoxy substituted starting materials can be prepared by alkylation of the corresponding hydroxy derivative using standard procedures, such as, reaction with alkylhalide in the presence of sodium carbonate. The appropriately substituted nitrobenzene derivatives described above in obtaining the carboxylic acid derivatives can be prepared by treating known di-substituted benzene compounds with nitric acid in the presence of sulfuric acid. The alkoxy substituted nitrobenzene derivatives can also be prepared by treating benzyloxyphenol (CA 73, P110139s) with an alkyl halide in the presence of a base to give the dialkoxy substituted benzene which can be nitrated by procedures described below. The trifluoromethyl sustituted starting materials can be prepared by the reaction of the corresponding benzoic acid derivatives with sulfur tetrafluoride and heating to give the substituted benzene derivatives which can be nitrated as described above, or a substituted nitrobenzoic acid can be treated with sulfur tetrafluoride with heating to give the corresponding trifluoromethyl substituted nitrobenzene derivative.

The following specific examples are illustrative of the invention.

EXAMPLE 1

2,3,4,4a,6,7,11b,12,13,13a-Decahydro-12-methyl-1H-dibenzo[a,f]quinolizin-13-one

A mixture of 16.75 g (0.1 mole) of 3,4-dihydroisoquinoline hydrochloride and 28.0 g of (0.2 mole) of 1-cyclohexen-1-yl ethyl ketone in 28 ml of ethanol is refluxed for 52 hours then poured into 300 ml of water and extracted with ether. The aqueous layer is separated and made basic by slowly adding ammonium hydroxide solution with stirring. Stirring is continued until a solid is formed after which the liquid is decanted. The solid is washed with water, dissolved in methylene chloride, dried over sodium sulfate and concentrated to an oil. The oil is dissolved in refluxing hexane, filtered, concentrated and cooled to give a solid which is recrystallized from hexane-benzene to give 2,3,4,4a,6,7,11b,12,13,13a-decahydro-12-methyl-1H-dibenzo[a,f]quinolizin-13-one, M.P. 144.5°–147.5°C.

EXAMPLE 2

2,3,4,4a,6,7,11b,12,13,13a-Decahydro-9,10-dimethyoxy-12methyl-1H-dibenzo[a,f]quinolizin-13-one When in Example 1 an appropriate amount of 3,4-dihydro-6,7-dimethoxyisoquinoline hydrochloride is substituted for 3,4-dihydroisoquinoline hydrochloride, 2,3,4,4a,6,7,11b,12,13,13a-decahydro-9,10-dimethoxy-12-methyl-1H-dibenzo[a,f]quinolizin-13-one is obtained.

EXAMPLE 3

2,3,4,4a,6,7,11b,12,13,13a-Decahydro-1H-dibenzo[a,f]quinolizin-13-one

When in Example 1 an appropriate amount of 1-cyclohexen-1-yl methyl ketone is substituted for 1-cyclohexen-1-yl ethyl ketone, 2,3,4,4a,6,7,11b,12,13,13a-decahydro-1H-dibenzo[a,f]quinolizin-13-one is obtained, M.P. 112°–140°C.

EXAMPLE 4

2,3,4,4a,6,7,11b,12,13,13a-Decahydro-9-methyl-1H-dibenzo[a,f]quinolizin-13-one when in Example 1 an appropriate amount of 3,4-dihydro-6-methylisoquinoline hydrochloride and 1-cyclohexen-1-yl methyl ketone are substituted for 3,4-dihydroisoquinoline hydrochloride and 1-cyclohexen-1-yl ethyl ketone respectively, 2,3,4,4a,6,7,11b,12,13,13a-decahydro-9-methyl-1H-dibenzo[a,f]quinolizin-13-one is obtained, M.P. 101°–121°C.

EXAMPLE 5

When in Example 1 the isoquinoline derivatives listed below are substituted for 3,4-dihydroisoquinoline hydrochloride and the ketone derivatives listed below are substituted for 1-cyclohexen-1-yl ethyl ketone the respective products listed below are obtained.

| Isoquinoline Hydrochloride Derivative | Ketone Derivative | Product |
| --- | --- | --- |
| 3,4-dihydro-7-hydroxyisoquinoline | 1-cyclopenten-1-yl benzyl ketone | 1,2,3,3a,5,6,10b,11,12,12a-decahydro-9-hydroxy-11-phenylbenzo[a]cyclopenta[f]quinolizin-12-one |
| 6,7-diethoxy-3,4-dihydroisoquinoline | 1-cyclopenten-1-yl methyl ketone | 1,2,3,3a,5,6,10b,11,12,12a-decahydro-8,9-diethoxybenzo[a]cyclopenta[f]quinolizin-12-one |
| 7-butoxy-3,4-dihydroisoquinoline | 1-cyclohexen-1-yl phenethyl ketone | 2,3,4,4a,6,7,11b,12,13,13a-decahydro-10-butoxy-12-benzyl-1H-dibenzo[a,f]quinolizin-13-one |
| 3,4-dihydro-7-n-hexylisiquinoline | 1-cyclohepten-1-yl methyl ketone | 1,2,3,4,5,5a,7,8,12b,13,14,14a-dodecahydro-11-n-hexylbenzo[a]cyclohepta[f]quinolizin-14-one |
| 6,8-dichloro-3,4-dihydroisoquinoline | 1-cyclohepten-1-yl methyl ketone | 1,2,3,4,5,5a,7,8,12b,13,14,14a-dodecahydro-10,12-dichlorobenzo[a]cyclohepta[f]quinolizin-14-one |

EXAMPLE 6

1,2,3,3a,5,6,10b,11,12,12a-Decahydrobenzo[a]cyclopenta[f]quinolizin-12-one

A mixture of 16.7 g (0.1 mole) of 3,4-dihydroisoquinoline hydrochloride and 22.0 g (0.02 mole) of 1-cyclopenten-1-yl methyl ketone in 22 ml of ethanol is refluxed overnight then evaporated to dryness. The remaining solid is dissolved in water and washed with ether. The aqueous layer is made basic with concentrated ammonium hydroxide solution with stirring. Upon the formation of an oil, ice is added to the solution after which a solid forms. The solid material is washed with water, dried overnight in a vacuum oven, and recrystallized from hexane to give 1,2,3,3a,5,6,10b,12,12a-decahydrobenzo[a]cyclopental[f]-quinolizin-12-one, M.P. 101°–102.5°C.

EXAMPLE 7

2,3,4,4a,6,7,11b,12,13,13a-Decahydro-9,10-dimethoxy-1H-dibenzo[a,f]quinolizin-13-one When in Example 6 appropriate amounts of 3,4-dihydro-6,7-dimethoxyisoquinoline hydrochloride and 1-cyclohexen-1-yl methyl ketone respectively are substituted for 3,4-dihydroisoquinoline and 1-cyclopenten-1-yl methyl ketone, 2,3,4,4a,6,7,11b,12,13,13a-decahydro-9,10-dimethoxy-1H-dibenzo[a,f]quinolizin-13-one is obtained, M.P. 129°–141°C.

EXAMPLE 8

2,3,4,4a,6,7,11b,12,13,13a-Decahydro-10-fluoro-1H-dibenzo[a,f]quinolizin-13-one

A mixture of 19.5 g (0.1 mole) of 3,4-dihydro-7-fluoroisoquinoline hydrochloride and 18.6 g (0.15 mole) of 1-cyclohexen-1-yl methyl ketone in 22 ml of ethanol is refluxed with stirring overnight then cooled to room temperature. The solution is poured into water, whereupon a suspension of undissolved material forms, and is extracted with ether. The aqueous layer and its suspended solid are stirred and treated with ammonium hydroxide solution to pH 8.5 to 9.0. The suspended solid is broken up, collected by decantation washed with water, dissolved in methylene chloride, dried over sodium sulfate and evaporated. The remaining residue is dissolved in benzene and chromatographed on alumina and eluted with benzene. The resulting solid is triturated with hexane and dried to give 2,3,4,4a,6,7,11b,12,13,13a-decahydro-10-fluoro-1H-dibenzo[a,f]quinolizin-13-one, M.P. 130°–136°C.

EXAMPLE 9

2,3,4,4a,6,7,11b,12,13,13a-Decahydro-10-chloro-1H-dibenzo[a,f]quinolizin-13-one

When in Example 8 an appropriate amount of 7-chloro-3,4-dihydroisoquinoline hydrochloride is substituted for 3,4-dihydro-7-fluoroisoquinoline hydrochloride, 2,3,4,4a,6,7,11b,12,13,13a-decahydro-10-chloro-1H-dibenzo[a,f]quinolizin-13-one is obtained.

EXAMPLE 10

1,2,3,3a,5,6,10b,11,12,12a-Decahydro-8,9-dimethoxybenzo[a]cyclopenta[f]quinolizin-12-one A mixture of 23.0 g (0.1 mole) of 3,4-dihydroisoquinoline hydrochloride, 23.0 g (0.2 mole) of 1-cyclopenten-1-yl methyl ketone in 25 ml of ethanol is refluxed overnight then evaporated in vacuo. The residual oil is partitioned between water and ether, then the aqueous layer is separated and washed with ether, made basic with concentrated ammonium hydroxide solution and stirred. A sticky solid material forms which is washed with water partially dried in vacuo, dissolved in methylene chloride, dried over sodium sulfate and evaporated. The residual material is dissolved in benzene and chromatographed on alumina eluting with benzene then with benzene ethyl acetate (85:15). The solid obtained is recrystallized from benzenehexane to give 1,2,3,3a,5,6,10b,11,12,12a-decahydro-8,9-dimethoxybenzo[a]cyclopenta[f]quinolizin-12-one, M.P. 105°–114°C.

EXAMPLE 11

When in Example 1, 25.5 g (0.1 mole) of 6,7-di-tert-butyl-3,4-dihydroisoquinoline hydrochloride is substituted for 3,4-dihydroisoquinoline, 2,3,4,4a,6,7,11b,12,13,13a-decahydro-9,10-di-tert-butyl-12-methyl-1H-dibenzo[a,f]quinolizin-13-one is obtained.

The 6,7-di-tert-butyl-3,4-dihydroisoquinoline hydrochloride starting material is prepared from ortho-di-tert-butylbenzene which is treated with nitric acid in acetic anhydride to give 3,4-di-tert-butylnitrobenzene. The di-substituted nitrobenzene derivative is hydrogenated over palladium to give the corresponding amine which is diazotized using nitrous acid and boron trifluoride to give the diazonium salt of 3,4-di-tert-butylaniline (Tetrahedron Letters, 1964(1), 61–64). The diazonium salt derivative is converted to the corresponding phenethylamine which is cyclized to the dihydroisoquinoline by the following reaction sequence.

M-750 CIP

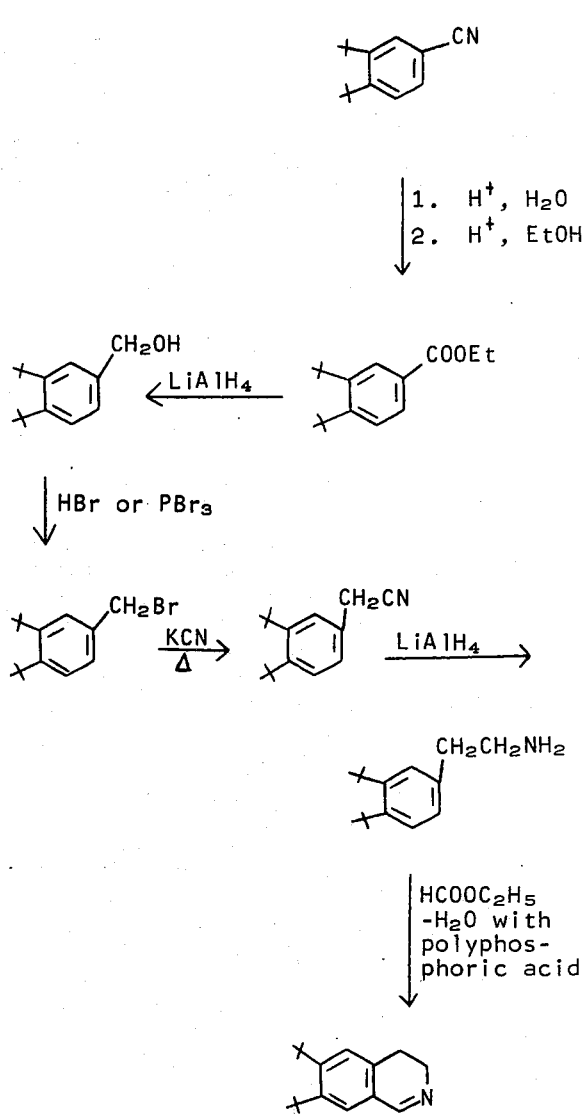

The compounds of this invention selectively remit reserpine induced extrapyramidal motor deficits, or catalepsy, induced in experimental animals rendering them useful as antidepressants, antiparkinson agents and useful in the treatment of catalepsy and Parkinsonian like effects resulting from the administration of neuroleptics. Administration of reserpine to mice, rats, cats and dogs results in motor disturbances of extrapyramidal origin which are generally referred to as catalepsy and also results in symptoms which closely resemble those of Parkinson's disease, that is, akinesia, rigidity and tremors. In cats and dogs the response is not uniform, but rather varies from a moderate tremor and ataxia to collapse resembling sleep. In addition there is a peripheral effect as evidenced in mice and rats by paralysis of the eye lid, or ptosis, and in cats and dogs by a paralysis of the nictitating membrane.

The ability of the compounds of this invention to selectively remit reserpine induced catalepsy, or motor deficits, is demonstrated by a reproducible restoration of motor activity without concurrent remission of such peripheral effects of reserpine as ptosis in rats and mice, or paralysis of the nictitating membrane in cats and dogs. For example, mice of the Swiss Webster strain weighing from 18 to 25 g are given intravenously 2 mg/kg of reserpine, and sixty minutes later the test compound is given orally. From 15 to 60 minutes after administration of the test compound observations as to the motor ability of the mouse and remission of ptosis are made. For example, oral administration in mice of 100 mg/kg of 1,2,3,3a,5,6,10b,11,12,12a-decahydro-8,9-dimethoxybenzo[a]cyclopenta[f]quinolizin-12-one results in the selective remission of central reserpine elicited deficits in 60% of the treated mice.

The compounds of this invention can be administered to animals, warm blooded animals and particularly mammals and humans either alone or in the form of pharmaceutical preparations which contain the novel compounds suitable for oral or parenteral administration. Pharmaceutical preparations containing compounds of this invention and conventional pharmaceutical carriers can be employed in unit dosage forms such as solids, for example, tablets and capsules, or liquid solutions, suspensions or elixirs for oral administration, or liquid solutions, suspensions, emulsions, and the like for parenteral administration. The quantity of compound administered can vary over a wide range to provide from about 0.1 mg/kg (milligram per kilogram) to about 100 mg/kg of body weight of the patient per day to achieve the desired effect. Unit doses of these compounds can contain from about 5 to 500 mg of The compound may be administered, for example from 1 to 4 daily.

I claim:

1. A process for the preparation of a compound of the formula

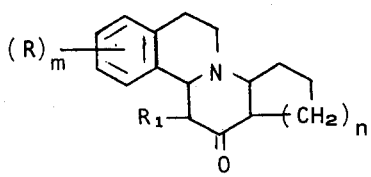

wherein R is selected from hydrogen, hydroxy, halogen, trifluoromethyl, a straight or branched lower alkyl group of from 1 to 6 carbon atoms, and a straight or branched lower alkoxy group of from 1 to 6 carbon atoms; $R_1$ is selected from hydrogen, a lower alkyl group of from 1 to 6 carbon atoms, phenyl, and benzyl; $m$ is an integer of 1 or 2; $n$ is an integer of from 1 to 3; and pharmaceutically acceptable salts, which comprises the steps of reacting a 3,4-dihydroisoquinoline of the formula

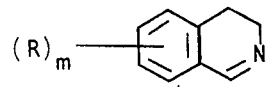

wherein R and $m$ have the meanings described hereinabove, with a cycloalk-1-enyl ketone of the formula:

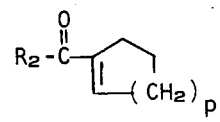

wherein $R_2$ is selected from a lower alkyl group of from 1 to 7 carbon atoms, benzyl or phenethyl; and $p$ is an integer of from 1 to 3, in the presence of a solvent selected from a lower alcohol, dimethyl formamide, dimethylsulfoxide, an aromatic solvent, and a halogenated hydrocarbon solvent.

2. A process of claim 1 wherein an acid catalyst is employed in the reaction.

3. A process of claim 2 wherein the solvent is a lower alcohol.

4. A process of claim 3 wherein the acid catalyst is hydrochloric acid.

5. A process of claim 1 wherein $m$ is the integer 1.

6. A process of claim 1 wherein the substituents on the 3,4-dihydroisoquinoline derivative as represented by R are attached at the 6 and 7- position of the dihydroisoquinoline.

7. A process of claim 6 wherein each of the substituents attached at the 6 and 7- positions is selected from hydrogen, chlorine, fluorine, bromine, iodine, hydroxy, straight or branched lower alkoxy of from 1 to 4 carbon atoms, straight or branched lower alkyl of from 1 to 4 carbon atoms and trifluoromethyl with the proviso that each of the substituents groups is not trifluoromethyl.

8. A process of claim 7 wherein the lower alkyl of from 1 to 4 carbon atoms is straight chained.

9. A process of claim 6 wherein the substituent attached at the 6- position of the dihydroisoquinoline derivative is hydrogen and the substituent attached at the 7- position of the dihydroisoquinoline is selected from hydrogen, chlorine, fluorine, bromine, iodine, hydroxy, straight or branched lower alkoxy of from 1 to 4 carbon atoms, straight or branched lower alkyl of from 1 to 4 carbon atoms and trifluoromethyl.

10. A process of claim 6 wherein the substituent attached at the 7- position of the dihydroisoquinoline is hydrogen and the substituent attached at the 6- position of the dihydroisoquinoline is selected from chlorine, fluorine, bromine, iodine, hydroxy, straight or branched lower alkoxy of from 1 to 4 carbon atoms, straight or branched lower alkyl of from 1 to 4 carbon atoms and trifluoromethyl.

* * * * *